(12) United States Patent
Simon

(10) Patent No.: US 8,283,167 B2
(45) Date of Patent: Oct. 9, 2012

(54) PREPARATION OF ANNEXIN DERIVATIVES

(75) Inventor: Jaime Simon, Angleton, TX (US)

(73) Assignee: Clear Vascular Inc., New York, NY (US)

( * ) Notice: Subject to any disclaimer, the term of this patent is extended or adjusted under 35 U.S.C. 154(b) by 296 days.

(21) Appl. No.: 12/700,312

(22) Filed: Feb. 4, 2010

(65) Prior Publication Data

US 2010/0204457 A1 Aug. 12, 2010

Related U.S. Application Data

(60) Provisional application No. 61/151,598, filed on Feb. 11, 2009.

(51) Int. Cl.
*C12N 5/87* (2006.01)
*C12N 5/071* (2010.01)
*A61K 38/00* (2006.01)

(52) U.S. Cl. .................. 435/375; 435/173.9; 530/355

(58) Field of Classification Search .................. None
See application file for complete search history.

(56) References Cited

U.S. PATENT DOCUMENTS

| | | | |
|---|---|---|---|
| 6,197,278 | B1 | 3/2001 | Blankenberg et al. |
| 6,843,980 | B2 | 1/2005 | Green |
| 7,115,248 | B2 | 10/2006 | Kasina et al. |
| 7,204,972 | B2 | 4/2007 | Tait et al. |
| 2003/0003048 | A1 | 1/2003 | Li et al. |
| 2003/0036699 | A1 | 2/2003 | Strauss |
| 2003/0152513 | A1 | 8/2003 | Blankenberg et al. |
| 2006/0009381 | A1 | 1/2006 | Reuteningsperger |
| 2007/0021641 | A1 | 1/2007 | Gonzales et al. |

OTHER PUBLICATIONS

Church et al. (1996) Single L-type calcium channel conductance with physiological levels of calcium in chick ciliary ganglion neurons, J. Physiol., vol. 496, pp. 59-68.*
Burger et al. (1993) A rapid and efficient purification method for recombinant annexin V for biophysical studies, FEBS Lett., vol. 329, No. 1-2, pp. 25-28.*
Florine et al. (1987) Protein Redistribution in Model Membranes: Clearing of M 13 Coat Protein from Calcium-Induced Gel-Phase Regions in Phosphatidylserine/Phosphatidylcholine Multilamellar Vesicles, Biochemistry, Vo.26, pp. 2978-2983.*
Neumann et al. (1994)Calcium-induced changes in annexin V behaviour in solution as seen by proton NMR spectroscopy, Eur. J. Biochem., vol. 225, pp. 819-825.*
Faib et al. (2008) Formation of irreversibly bound annexin A1 protein domains on POPC/POPS solid supported membranes, Biochem. Biophys. Acta, vol. 1778, pp. 1601-1610.*
MACS (2004) "Cell Isolation Kits", Miltenyi Biotech,//www.miltenyibiotec.com/download/datasheets_en/118/MiltenyiBiotec_DataSheet_Annexin-V-MicroBead-Kit_130-090-201.pdf pp. 1-3.*
Richter et al. On the Kinetics of Adsorption and Two-Dimensional Self-Assembly of Annexin A5 on Supported Lipid Bilayers, Biophysical Journal, 2005, vol. 89, pp. 3372-3385, entire document, especially: Abstract; p. 3374, col. 2, para 4-7; p. 3374, col. 1, para 2, relevant to claims 1-14.
International Search Report and Written Opinion, mailed Apr. 12, 2010.

* cited by examiner

*Primary Examiner* — Anand Desai
*Assistant Examiner* — Samuel Liu
(74) *Attorney, Agent, or Firm* — Wood, Herron & Evans, LLP

(57) ABSTRACT

Labeled annexin is formed by reacting annexin or a modified annexin with a phosphatidylserine group or an analogue of phosphatidylserine. This phosphatidylserine annexin conjugate is then reacted with an appropriate label to form a labeled annexin and the annexin is separated from the phosphatidylserine group. The reaction between the phosphatidylserine group and the annexin is calcium ion concentration dependent. Therefore, the reaction can be promoted by having a high calcium ion concentration and the separation of the phosphatidyl group from the annexin group is facilitated by reducing the calcium ion concentration preferably by addition of an appropriate calcium chelating agent.

8 Claims, No Drawings

PREPARATION OF ANNEXIN DERIVATIVES

RELATED APPLICATION

This application is related to and claims the benefit of U.S. Provisional Patent Application Ser. No. 61/151,598, filed Feb. 11, 2009, the disclosure of which is incorporated herein by reference.

BACKGROUND OF THE INVENTION

During cell death or apoptosis, cells express phosphatidylserine. This compound has a serine group attached to two long hydrocarbon groups. It is known that annexin, or modified annexins, will preferentially bind to the serine of phosphatidylserine.

Accordingly, annexin has been used to target a variety of apoptotic cells for both therapeutic and imaging purposes. An appropriate therapeutic or imaging agent is attached to the annexin which then can be injected into a subject. In the bloodstream, the modified annexin will preferentially bind to the apoptotic cells, providing either a means to provide therapy to the individual or enable imaging of the apoptotic region.

By way of background, annexin is a protein with about 300 amino acids. There are a variety of different annexins. In particular, annexin-V, which has 319 amino acids, binds with high affinity to phosphatidylserine. The annexin binds to phosphatidylserine in a calcium dependent manner.

In order to utilize the annexin to deliver either the therapeutic or imaging agent to the apoptotic cell, the imaging agent or therapeutic compound, referred to as a payload, must be attached to the annexin. Annexin has multiple lysine groups that have pendent amine groups that are available for derivation. However, the ability of the annexin to attach to the phosphatidylserine is greatly diminished if too many lysine groups are derivatized. Thus, by labeling the annexin, its affinity to phosphatidylserine can be reduced.

In many applications, this may not be an extreme problem in that excess labeled annexin can be administered. However, in particular, with radiopharmaceuticals, the amount of radioactive material that can be administered to a patient is limited. Therefore, it is imperative that the binding affinity of the labeled annexin be maximized. This is also preferred in virtually any application that relies on annexin's affinity for phosphatidylserine.

SUMMARY OF THE INVENTION

The present invention is premised on the realization that the binding affinity of annexin for phosphatidylserine can be maintained during any labeling procedure by first binding the annexin to a phosphatidylserine moiety or analogue and subsequently reacting the annexin with the payload. After the annexin payload compound is formed, the phosphatidylserine-like group can be decoupled from the annexin and the labeled annexin can be recovered for use.

As the reaction between annexin and phosphatidylserine is mediated by calcium concentration, the annexin can be easily separated from the phosphatidylserine by complexing available calcium from the annexin/phosphatidyl solution. In particular, this can be done by simply adding a chelating agent that binds to the calcium in solution.

As phosphatidylserine is not itself soluble in aqueous solutions, the phosphatidyl group can be added as a phosphatidylserine derivative. In other words, the elongated hydrocarbon groups attached to the phosphatidyl group can be shortened, making the composition water soluble. In an alternate embodiment phosphatidylserine or a derivative thereof can be bonded to a solid support, such as a reverse phase C-18 resin. The solid phase can be combined with the annexin in an aqueous solution and subsequently labeled. The labeled annexin is separated from the phosphatidylserine on the solid support and can be used for the desired therapeutic or imaging purpose.

The objects and advantages of the present invention will be further appreciated in light of the following detailed description.

DETAILED DESCRIPTION

According to the present invention, annexin or a modified annexin is first bonded to a phosphatidylserine like moiety and subsequently reacted with a payload. Subsequent to this reaction the annexin is separated from the phosphatidylserine and used for medical purposes.

Annexin is a class of compounds characterized by the ability to bind with high affinity to membrane lipids in the presence of millimolar concentrations of calcium. Annexins have been shown to exhibit anti-coagulatory effects that are mediated by the binding of annexins to negatively charged surface phospholipids (e.g., on activated platelets). This annexin-phospholipid binding is believed to block the activation of clotting factors by such negatively charged surface phospholipids. Prior to the recognition of the annexin class of molecules, members thereof were also referred to in the literature as placental anticoagulant proteins (e.g., PAP-1, 2, 3 and 4), lipocortins, calpactins, vascular anti-coagulant (alpha and beta), calphobindin I, placental protein 4 (PP4), endonexin II, anchorin CII, calcium-dependent phospholipid binding protein, and the like. Annexin-V is a prototypical annexin molecule used in the description of the present invention. The term annexin includes native annexin purified from natural sources such as e.g. human placenta, or annexin molecules containing a native sequence produced through, e.g., genetic engineering, recombinant, or other means. The term annexin, unless otherwise specified, includes modified annexins as defined below, derived from or produced by any source.

Modified annexin is a molecule wherein the native sequence or molecule is altered in such a way without materially altering the membrane binding affinity of the annexin. Such annexins can be produced by chemical, genetic engineering or recombinant techniques as know to those of ordinary skill in the art. The modification can include a modification of the sequence through the addition of several amino acid residues, and/or an addition/deletion of an amino acid at a single site on the native or genetically engineered sequence. For example, the annexin can be modified at the N-terminus by the addition of amino acid residues, wherein at least one of the amino acids provides an accessible sulfhydryl group. The accessible sulfhydryl group or groups may be utilized during conjugation or remain available for further conjugation. The term modified annexin includes annexin multimers.

Annexin multimers are a combination of two or more monomeric modified annexin molecules of which the components of the multimer may be native or recombinant, or in any combination thereof; resulting in similar or improved membrane binding affinity over the monomeric annexin. A multimer composed of up to about 20 modified annexins is useful for the present invention. One example of an annexin multimer is an annexin dimer, which can be composed of two modified annexins linked by disulfide bonds between accessible sulfhydryl groups on the modified annexins. The annexin dimer can be produced directly as a fusion protein using known expression systems, wherein the two annexin molecules can be connected by a peptide linker through the accessible sulfhydryl groups. A dimeric molecule could contain additional functional sites, such as an endogenous radiolabel chelation site or an accessible sulfhydryl group for the attachment of one or more hexose residues, for example.

Other modified annexins are disclosed, for example, in Reutelingsperger, US Published Application 2006/0009381 and Tait et al., U.S. Pat. No. 7,204,972.

The annexin will be reacted with a payload or label. These payloads can be used for either therapeutic purposes and/or diagnostic purposes.

Therapeutic compounds can be, for example, a toxin, an enzyme, a lipid, a carbohydrate, an immunoglobulin or a fragment thereof, an immunoconjugate, a chemotherapeutic compound, a photosensitizer, a radionuclide, a cell death inducing agent, a cell death inhibiting agent, a fibrinolytic compound, and a combination thereof. Exemplary toxins are Dt, PE, P38, P40, ricin, abrin, diphtheria toxin, cholera toxin, gelonin, pseudomonas exotoxin, shigella toxin, and pokeweed antiviral protein. Exemplary enzymes are peroxidases, alkalases, and caspases.

Lipids are, for example, phospholipids, fatty acids, prenelenes, and steroids. A lipid can be embedded in the membrane of a liposome. Exemplary chemotherapeutic compounds are BiCNU, bleomycin, busulfan, CCNU, carboplatin, carboplatinum, carmustine, cisplatin, cisplatinum, chlorambucil, 2-cholrodcoxyadenosine, cladribine, cytarabine, cyclophosphamide, dacarbazine, daunorubicin, docetaxel, doxorubicin, DTIC, etoposide, 5-flourouracil, fludarabine, gemcitabine, hydroxyurea, idarubicin, ifosfamide, irinotecan, lomustine, melphelan, methotrexate, mithramycin, mitomycin, mitoxantrone, nitrogen mustard, oxaliplatin, paclitaxel, plicamycin, procarbazine, raltitrexed, semustine, tomudex, topotecan, vinblastine, vincristine, and vinorelbine. Therapeutic radionuclides are, for example, Iodine-131, Rhenium-186, Rhenium-188, Strontium-89, Samarium-153, Lutetium-177, Holmium-166, Actinium-225, Yttrium-90 and Sn-117m. Photosensitizers are, for example, phtaiocyanines, rhodoporphyrins, rhodochlorins, mesorhodochlorins, phyllocrythrin and its derivatives, porphorin and its derivatives, and metal-pyrollic compounds.

Examples of cell death inducing agents are apoptosis inducers, kinase inhibitors, activators of mitochondrial permeability transition, polynucleotides encoding for a cell death inducing protein, activators of ion-transport across the membrane, polynucleotides being an anti-sense to polynucleotides encoding for cell death inhibiting proteins, and polynucleotides interacting with and inhibiting cell death inhibiting proteins. Cell death inhibiting agents are, for example, apoptosis inhibitors, caspase inhibitors, cathepsin inhibitors, inhibitors of ion-transport across the membrane, inhibitors of mitochondrial permeability transition, growth factors, polynucleotides encoding for cell death inhibiting proteins, polynucleotides being an anti-sense to polynucleotides encoding for call death inducing proteins, and polynucleotides interacting with and inhibiting cell death inducing proteins.

Diagnostic compounds include, for example, a fluorescent group, a contrast agent, a photosensitizer, a radionuclide, an ultrasound agent, and a combination thereof. Exemplary fluorescent groups are Fluorescein-isothiocyanate ("FITC"), Oregon green, alexa, phycoerythrine, cy-compounds, propidium iodide, 7-AAD, sytox-compounds, and nanocrystals, such as Cadmium-Selenide, Lead-Selenide, Indium-Phosphide, and Gallium-Arsenide. Contrast agents are, for example, gadolinium chelates, magnetic particles, paramagnetic particles, and air bubbles. Photosensitizers include phthalocyanines, rhodoporphyrins, rhodochlorins, mesorhodochlorins, phyllocrythrin and its derivatives, porphorin and its derivatives, and metal-pyrollic compounds. Diagnostic radionuclides are, for example, carbon-11, fluorine-18, indium-111, iodine 123, iodine-131, nitrogen-13, oxygen-15, technetium-99m, zirconium-89, and a combination thereof.

One commonly used diagnostic payload is technetium 99m. Certain compounds are suitable for both therapeutic and diagnostic purposes. For example, radioisotopes that are conversion electron emitting sources can be used both to diagnose and treat. In particular, tin 117m is particularly suited for detecting and treatment of atherosclerotic plaque. Other payloads are disclosed, for example in Blankenberg et al., U.S. Pat. No. 6,197,278 and Tait, U.S. Pat. No. 7,204,972, the disclosures of which are hereby incorporated by reference.

Prior to bonding the selected payload to the annexin, the annexin is bonded to a phosphatidylserine. This reaction can be conducted either on a solid support or in a solution. The phosphatidylserine itself has two relatively long hydrocarbon chains which make the phosphatidylserine insoluble in aqueous solutions. In order to conduct a reaction in an aqueous solution, a phosphatidylserine analogue must be utilized. There are various water soluble phosphatidylserine compounds that can be purchased. Such agents include 1,2-dihexanoyl-sn-glycero-3-phospho-L-serine (sodium salt), 1,2-dioctanoyl-sn-glycero-3-phospho-L-serine (sodium salt), both available from Avanti Polar Lipids, Inc. In this application, the term "phosphatidylserine" specifically includes phophatidylserine analogues which retain their binding affinity to annexin.

The liquid phase reaction is conducted in a solution that has a high concentration of calcium ions. Generally, the calcium ion concentration of the solution must be at least about the concentration of calcium in blood or about 1 mM. At a concentration less than the physiological calcium concentration in blood, the annexin will not react with the phosphatidylserine.

The reaction is conducted by simply combining the calcium ion source, the annexin and the water soluble phosphatidylserine. There should be at least equal molar amounts of the phosphatidylserine compound and the annexin, with excess phosphatidylserine groups on a molar basis preferred, These components are combined at a temperature of about 37° C. for a period of about 15-30 minutes. This forms a complex of phosphatidylserine and annexin.

The annexin-phosphatidylserine complex is then reacted with the appropriate payload to form a labeled annexin according to the well known procedures. In particular, annexin can be labeled with either technetium 99m or tin 117m, using appropriate bifunctional chelating agents. For example, labeling of Sn-117m can be accomplished by adding phosphatidyl annexin complex to M-1,4,7,10 tetraacylododecane 1,4,7,10 tetraaceticacid isothiocyanato (M-DOTA-NCS)—(where M is the metallic radionuclide such as Sn-117m) at a pH of 9 at 37° C. for 1.5 hours. This will cause the isothiocyanato group on the bifunctional chelating agent to react with available lysines on the annexin, and bind the radionuclide to the annexin.

This is merely exemplary. Other payloads can be bonded to the annexin using well known procedures, such as those disclosed in U.S. Pat. Nos. 6,197,278; 7,115,248; and 7,204,972, the disclosures of which are incorporated herein by reference.

Upon completion of the labeling reaction, the annexin is separated from the phosphatidylserine by removing calcium from the solution by adding a chelating agent that binds the calcium. In particular, adding sufficient EDTA to bind calcium in the solution will cause the phosphatidylserine to separate from the annexin. The annexin can then be separated from the solution by chromographic separation techniques, such as size exclusion chromatography.

In the solid phase reaction, the phosphatidylserine is bonded to a solid support. One particular solid support is a lipophillic reverse phase C-18 resin commonly used in chromographic procedures. The phosphatidylserine or analogue in the desired concentration is dissolved in an appropriate organic solvent, such as lower molecular weight ether or other volatile solvent and coated onto the reverse phase resin. The phosphatidylserine will naturally bind to the resin. The solvent is removed by evaporation. The resin, usually in the form of beads, is then added to an aqueous solution containing calcium ions and annexin. The same procedure as the liquid phase reaction is followed. Upon completion of the reaction of the annexin with the appropriate payload, the labeled annexin is separated from the phosphatidylserine bonded to the resin by addition of EDTA. This will cause the labeled annexin to separate from the phosphatidylserine and the annexin can then be separated from the beads by filtration.

The labeled annexin formed using this method retains a greater percentage of its unlabeled binding affinity for phosphatidylserine, maximizing the efficacy of the labeled annexin either as a therapeutic agent of an imaging agent. This method should also make more lysines available to bond to payloads increasing the number of payloads for a single annexin. This will allow a lesser amount of annexin to be used to provide the same benefits.

This has been a description of the present invention along with the preferred method of practicing the present invention. However, the invention itself should only be defined by the appended claims.

What is claimed is:

1. A method of preparing annexin V bound payload compound comprising steps in the following order:
   binding said annexin V to phosphatidylserine to form a phosphatidylserine annexin V complex having the annexin V moiety and the phosphatidylserine moiety in the presence of concentration of calcium ions of at least 1 mM;
   binding said payload to said annexin V moiety of said phosphatidylserine annexin V complex; and
   separating said payload and said annexin V moiety from said phosphatidylserine moiety thereby to form said annexin V bound payload compound.

2. The method claimed in claim 1 wherein said phosphatidylserine is a phosphatidylserine analogue.

3. The method claimed in claim 1 wherein said annexin is an annexin V dimer.

4. The method claimed in claim 1 wherein said annexin is a multimer.

5. The method claimed in claim 1 wherein said phosphatidylserine is bonded to a solid support and wherein said phosphatidylserine annexin V complex is formed on said solid support.

6. The method claimed in claim 1 wherein said phosphatidylserine is bound to said annexin in the presence of calcium-ion concentration of at least about 1 mM and wherein said annexin V moiety is separated from said phosphatidylserine moiety by reducing the calcium-ion concentration.

7. The method claimed in claim 6 wherein said calcium-ion concentration is decreased to less than 1 mM in said separating step by chelating said calcium ions.

8. The method claimed in claim 1 wherein said annexin moiety is separated from said phosphatidylserine moiety by chromatography.

* * * * *